United States Patent
Mammadov et al.

(10) Patent No.: US 9,745,235 B2
(45) Date of Patent: Aug. 29, 2017

(54) METHOD FOR HYDROGENATION OF $CO_2$ IN ADIABATIC METAL REACTORS

(71) Applicant: SAUDI BASIC INDUSTRIES CORPORATION, Riyadh (SA)

(72) Inventors: Aghaddin Kh. Mammadov, Houston, TX (US); Clark David Rea, Houston, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 15/034,937

(22) PCT Filed: Nov. 6, 2014

(86) PCT No.: PCT/US2014/064248
§ 371 (c)(1),
(2) Date: May 6, 2016

(87) PCT Pub. No.: WO2015/069840
PCT Pub. Date: May 14, 2015

(65) Prior Publication Data
US 2016/0272562 A1   Sep. 22, 2016

Related U.S. Application Data

(60) Provisional application No. 61/902,542, filed on Nov. 11, 2013.

(51) Int. Cl.

| | | |
|---|---|---|
| C07C 29/151 | (2006.01) | |
| C10K 3/06 | (2006.01) | |
| C01B 3/58 | (2006.01) | |
| B01J 19/02 | (2006.01) | |
| C01B 3/16 | (2006.01) | |
| B01J 33/00 | (2006.01) | |
| B01J 23/34 | (2006.01) | |
| B01J 37/30 | (2006.01) | |
| C01B 31/18 | (2006.01) | |
| B01J 23/24 | (2006.01) | |
| B01J 8/02 | (2006.01) | |
| C10K 3/02 | (2006.01) | |
| B01J 37/20 | (2006.01) | |
| B01J 23/14 | (2006.01) | |
| B01J 23/22 | (2006.01) | |

(52) U.S. Cl.
CPC ............ *C07C 29/1518* (2013.01); *B01J 8/02* (2013.01); *B01J 19/02* (2013.01); *B01J 33/00* (2013.01); *C01B 3/16* (2013.01); *C01B 3/58* (2013.01); *C10K 3/026* (2013.01); *C10K 3/06* (2013.01); *B01J 23/14* (2013.01); *B01J 23/22* (2013.01); *B01J 23/24* (2013.01); *B01J 23/34* (2013.01); *B01J 37/20* (2013.01); *B01J 2219/0286* (2013.01); *C01B 31/18* (2013.01); *C01B 2203/0435* (2013.01); *C01B 2203/0475* (2013.01); *C01B 2203/061* (2013.01); *Y02P 20/52* (2015.11)

(58) Field of Classification Search
CPC ..... C01B 3/16; C01B 3/58; C01B 2203/0435; C01B 2203/0475; C01B 2203/061; C01B 31/18; C07C 29/1518; B01J 8/02; B01J 33/00; B01J 19/02; B01J 37/20; B01J 23/14; B01J 23/22; B01J 23/24; C01K 3/026; C01K 3/06
See application file for complete search history.

(56) References Cited

U.S. PATENT DOCUMENTS

| | | |
|---|---|---|
| 7,041,621 B2 | 5/2006 | Ramani et al. |
| 7,790,776 B2 | 9/2010 | Christensen et al. |
| 7,932,298 B2 | 4/2011 | Young |
| 8,288,446 B2 | 10/2012 | Mamedov et al. |
| 8,551,434 B1 | 10/2013 | Mammadov et al. |
| 2005/0118089 A1 | 6/2005 | Abbott et al. |
| 2005/0265920 A1 | 12/2005 | Ercan et al. |
| 2008/0313962 A1 | 12/2008 | Abbott et al. |
| 2010/0168257 A1 | 7/2010 | Duisberg et al. |
| 2010/0190874 A1 | 7/2010 | Mamedov et al. |
| 2011/0114504 A1 | 5/2011 | Sivasankar et al. |
| 2012/0231948 A1 | 9/2012 | Saito |
| 2013/0072583 A1 | 3/2013 | Koskinen et al. |
| 2013/0116345 A1 | 5/2013 | Pansare et al. |

OTHER PUBLICATIONS

Rostrup-Nielsen, sulfur-passivated nickel catalystfor carbon free steam reforming, Journal of Catalysis 85, 31-43 (1984).*
Doty et al., new paradigms for standard liquid fuels from O2, H2O, CH4, and off peak energy, (American Chemical Society, Division of Fuel Chemistry 2010, 55 (1)).*
FR2921055 A1; English Abstract Only; Date of Publication Mar. 20, 2009; 2 pages.
International Search Report for International Application No. PCT/US2014/064248; International Filing Date Nov. 6, 2014; Date of Mailing Feb. 13, 2015; 5 pages.
JP 04377699 B2; English Abstract Only; Date of Publication Dec. 2, 2009; 1 page.
JP 04377700 B2; English Abstract Only; Date of Publication Dec. 2, 2009; 1 page.
JP 2010194534 A; English Abstract Only; Date of Publication Sep. 9, 2010; 1 page.
WO 2012153762 A1; English Abstract Only; Date of Publication Mar. 20, 2009; 1 page.
Written Opinion of the International Search Report for International Application No. PCT/US2014/1064248; International Filing Date Nov. 6, 2014; Date of Mailing Feb. 13, 2015; 5 pages.

* cited by examiner

*Primary Examiner* — Jafar Parsa
(74) *Attorney, Agent, or Firm* — Cantor Colburn LLP

(57) ABSTRACT

In an embodiment: a method of making syngas in a metal reactor can comprise introducing carbon dioxide and hydrogen to the metal reactor in the presence of a catalyst to form the syngas, wherein the metal reactor comprises nickel and wherein the carbon dioxide and the hydrogen are in physical contact with a wall of the metal reactor; and passivating the nickel with a sulfur containing compound.

20 Claims, No Drawings

METHOD FOR HYDROGENATION OF $CO_2$ IN ADIABATIC METAL REACTORS

CROSS REFERENCE TO RELATED APPLICATIONS

This application is a National Stage application of PCT/US2014/064248, filed Nov. 6, 2014, which claims the benefit of U.S. Provisional Application No. 61/902,542, filed Nov. 11, 2013, both of which are incorporated by reference in their entirety herein.

TECHNICAL FIELD

This Application relates to a method for the hydrogenation of carbon dioxide ($CO_2$) in an adiabatic reactor.

BACKGROUND

Synthetic gas (also referred to herein as syngas), is a gaseous mixture containing hydrogen ($H_2$) and carbon monoxide (CO), which can further comprise other gas components such as one or more of carbon dioxide ($CO_2$), water ($H_2O$), methane ($CH_4$), nitrogen ($N_2$). In the past decades, numerous processes have been developed to produce syngas due to its successful use as synthetic fuel and also in a number of chemical processes, such as synthesis of methanol, ammonia, Fischer-Tropsch type synthesis and other olefin syntheses, hydroformylation reactions, carbonylation reactions, reduction of iron oxides in steel production, etc.

Natural gas and (light) hydrocarbons are the predominant starting material for making syngas. For example, syngas can be produced using methane as the dominate feedstock, by steam reforming, partial oxidation, $CO_2$ reforming, or by a so-called auto-thermal reforming reaction. One of the disadvantages associated with syngas production by steam reforming of methane, which is the most widely applied process to produce syngas, is that the composition of the produced gas mixture is limited by the reaction stoichiometry to $H_2/CO$ ratios of 3 or higher.

In order to avoid such drawbacks and to help counteract increasing carbon dioxide ($CO_2$) concentrations in the atmosphere, research has been conducted to manufacture syngas from $CO_2$ as a raw material. The conversion is based on an equilibrium reaction, reaction 1:

$$CO + H_2O \leftrightarrows CO_2 + H_2 \quad (1)$$

The forward reaction is known as the water gas shift (WGS) reaction, while the reverse reaction is known as the reverse water gas shift (RWGS) reaction.

There remains a need in the art for improved processes for the conversion of $CO_2$ to syngas.

BRIEF DESCRIPTION

Disclosed herein are methods for making syngas.

In an embodiment: a method of making syngas in a metal reactor can comprise introducing carbon dioxide and hydrogen to the metal reactor in the presence of a catalyst to form the syngas, wherein the metal reactor comprises nickel and wherein the carbon dioxide and the hydrogen are in physical contact with a wall of the metal reactor; and passivating the nickel with a sulfur containing compound.

The above described and other features are exemplified by the following detailed description.

DETAILED DESCRIPTION

The conversion of $CO_2$ to syngas is currently performed in glass or quartz reactors under isothermal conditions due to methane and coke formation that arises when the reaction is performed in a metal reactor. The Applicants discovered that the conversion could occur in a metal reactor (such as one comprising stainless steel) under, for example, adiabatic conditions, but discovered that after an amount of time, for example, after 3 months, of reacting in the metal reactor, formation of coke and methane was observed. They also found that when pressure in the reactor is greater than atmospheric, for example, greater than or equal to 10 pounds per square in gauge (psig) (69 kiloPascal (kPa)) coke formation increased. The Applicants discovered a pressure drop due to the coke formation on the reactor walls and developed a procedure to remove the coke build-up comprising treating the reactor with a sulfur stream comprising a sulfur compound to passivate the reactor walls and optionally introducing an oxygen containing stream at an elevated temperature in order to burn off any coke that has accumulated on the reactor walls.

The conversion of $CO_2$ to syngas can occur by introducing a $CO_2$ stream and a $H_2$ stream to a metal reactor to produce a gas mixture comprising carbon monoxide, water, and possibly un-converted carbon dioxide, and un-converted hydrogen. Likewise, the $CO_2$ and the $H_2$ can be introduced to the metal reactor as a single stream. This reaction can occur in the presence of excess hydrogen, for example, by the following reaction 2:

$$CO_2 + nH_2 \leftrightarrow CO + (n-1)H_2 + H_2O \quad (2)$$

where n is greater than 1, preferably, 2 to 10. The reaction can be shifted to the right by removing the water, for example, by condensation, liquid/gas separation, and the like.

The carbon dioxide that is introduced to the metal reactor can originate from various sources. For example, the carbon dioxide can originate from a waste gas stream, e.g., from a plant on the same site, such as from ammonia synthesis, or after recovering the carbon dioxide from a gas stream. The gas composition of these carbon dioxide streams can optionally be adjusted via non-catalytic means prior to use in the present conversion process. Furthermore, at least an amount of the carbon dioxide introduced to the metal reactor can be un-reacted carbon dioxide from the present $CO_2$ conversion reaction, i.e., recycled.

The amount of hydrogen introduced to the metal reactor can vary widely. For example, the amount of hydrogen introduced to the metal reactor can be such that the value of n in equation 2 is 1 to 10, preferably, 2 to 6. Likewise, the amount of hydrogen introduced to the metal reactor can be such that syngas produced has a $H_2:CO$ ratio of 0.1 to 10, preferably, 1 to 8, more preferably, 4 to 6.

The produced syngas can be further employed as a feedstock in different conversion processes, such as methanol formation, olefin synthesis (such as that via Fischer-Tropsch catalysis), reduction of iron oxide in steel production, oxosynthesis, aromatics production, hydrocarbonylation reactions (such as methanol carbonylation and olefin carbonylation), etc. For example, if the feed gas contains $CO_2$ and $H_2$ in molar ratio of 1:2 (n=2 in above equation), the produced syngas can have a $H_2:CO$ ratio of about 1, which can be used for producing oxygenates. Likewise, if the feed gas contains $CO_2$ and $H_2$ in molar ratio of 1:3 (n=3 in above equation), the produced syngas can have a $H_2:CO$ ratio of about 2, which can be useful in olefin or methanol synthesis processes.

The produced syngas can be combined with a different syngas source and/or with a product from a separate reaction. For example, the produced gas mixture can be combined with a product from the steam reforming of an alkane (e.g., methane) or dry reforming of an alkane (also called $CO_2$ reforming), e.g., for converting the feed stream into methanol or other chemical products. When the present process of converting $CO_2$ to syngas is combined with a methanol synthesis reaction, a purge gas from the methanol synthesis reaction, containing hydrogen and carbon dioxide can be recycled back to the carbon dioxide hydrogenation step and, optionally, at least some of the heat produced in the exothermic methanol synthesis step can be utilized in the endothermic RWGS step.

A catalyst can be employed in the conversion of the $CO_2$ to syngas. The catalyst can comprise a metal oxide catalyst (MeOx). The metal can comprise chromium (Cr), manganese (Mn), tin (Sn), tungsten (W), vanadium (V), molybdenum (Mo), lanthanum (La), cesium (Ce), lead (Pb), magnesium (Mg), calcium (Ca), potassium (K), tungsten (W), copper (Cu), or a combination comprising one or more of the foregoing. The metal can include a first metal such as an element selected from: Cr, Mn, Sn, W, V, and Mo and a second metal such as La, Ce, Pb, and/or Mg. The catalyst can comprise 5 to 60 weight percent (wt %), preferably, 5 to 40 wt %, more preferably, 15 to 25 wt % of metal oxide, based on the total weight of metal oxide and support. The catalyst can comprise an inert support, such as a silica, $Al_2O_3$, MgO, titania, zirconia, or the like. The catalyst can comprise a chromium oxide catalyst and an aluminum oxide support. The catalyst can be free of nickel. For example, the only nickel present would be as an impurity in the catalyst materials. In other words, the catalyst can comprise less than or equal to 0.1 wt % of nickel, preferably, less than or equal to 0.05 wt % nickel, and more preferably 0 wt % nickel, based on the total weight of the catalyst.

The catalyst can be a formed catalyst and can be prepared by methods such as pelletizing, tableting, and/or extruding the support and optionally the chromium into a shape such as a sphere, a tablet, a pellet, a ring, an extrudate, or the like. If the metal is not present during forming, then the metal can be added (e.g., impregnated into) the support. The formed catalyst can then be dried and/or calcined. The formed catalyst can be a sphere with an average diameter of, for example, 5 micrometers to 15 mm. The formed catalyst can be an extrudate with a diameter of, for example, 0.5 to 10 millimeters (mm) with a length of, for example, 1 to 15 mm.

The $CO_2$ conversion reaction can occur under adiabatic conditions at a temperature suitable for the conversion reaction. For example, the reactant stream(s) (herein the reactant stream(s) refers to either a separate $CO_2$ stream and a separate $H_2$ stream or a combined $CO_2/H_2$ stream) can enter the metal reactor at a temperature of 650 to 800 degrees Celsius (° C.), preferably, 700 to 800° C., more preferably, 730 to 750° C. When the temperature of the inlet gas(s) is 730 to 750° C., the outlet gas(s) can be at a temperature of 560 to 580° C., resulting in a $CO_2$ conversion of about 60%. At this conversion, the resulting syngas can comprise, for example, about 14 volume percent (vol %) CO, about 78 vol % hydrogen, and about 8 vol % $CO_2$ based on the total volume of the CO, $H_2$, and $CO_2$.

The $CO_2$ conversion reaction can occur over a wide range of pressures. For example, the pressure can be 0.1 to 6 MPa, preferably, 1.5 to 5 MPa, more preferably, 2 to 4 MPa. The $CO_2$ conversion reaction can occur at atmospheric pressure.

The contact time in the step of contacting the gaseous feed mixture containing carbon dioxide and hydrogen with a catalyst can vary widely. Preferably, the contact time can be 0.5 to 6 seconds (s), preferably, 1.5 to 5 s, more preferably, 2 to 4 s.

The process occurs in a metal reactor such that the $CO_2$ conversion reaction is in physical contact with the metal in the reactor. In other words, the reactor is free of a coating, such as a quartz or glass coating, that would otherwise prevent or reduce the $CO_2$ conversion reaction from coming in contact with the metal. The metal reactor can comprise an amount of nickel. For example, the metal reactor can comprise 0.1 to 20 wt % nickel, preferably, 1 to 15 wt %, more preferably, 5 to 10 wt %. The metal can be stainless steel (SS), for example, SS 316 or SS 304. The reactor type can be, for example, a continuous fixed bed reactor.

The presence of nickel in the reactor walls can result in the formation of coke on the reactor walls, where the nickel can react with CO in the reactor to form nickel carbide and nickel oxide via the following reaction 3:

$$CO + 2Ni \rightarrow Ni^+C + NiO \qquad (3)$$

It is noted that the nickel carbide can further react with hydrogen to form methane and nickel, resulting in a further loss of CO product. As the $CO_2$ conversion reaction proceeds, the nickel carbide, aka coke, begins to build-up on the reactor walls. It is noted that there is little to no build-up of coke on the catalyst. With time, the coke build-up results in a drop in pressure in the reactor and a decrease in reaction conversion.

In order to prevent or reduce the amount of coke build-up on the reactor walls, the Applicants found that they could passivate the nickel with a sulfur containing compound (such as hydrogen sulfide and/or methyl sulfide) by introducing a sulfur stream comprising the sulfur containing compound to the reactor. The sulfur in the sulfur containing compound reacts with the nickel in the reactor wall to produce nickel sulfide. At this time, the reactant stream(s) can be turned off and the reactor can be free of a catalyst. The passivating can occur for 4 to 24 hours, preferably, 8 to 24 hours. After the passivating, the sulfur stream can be turned off and the reactant stream(s) can be turned back on. The passivating can occur prior to the introduction of the reactant stream(s), referred to as "initial passivating." The passivating can occur repeatedly after an amount of reaction time, referred to as "intermittent passivating," for example, every three months. The intermittent passivating can occur, for example, when the concentration of methane in the products is greater than or equal to 1 mole % as such a concentration can form from intermediate coke fragments.

During or after the intermittent passivating, the coke that has formed on the reactor walls can be burned off by introducing an oxygen containing stream, such as pure oxygen or air, to the reactor at an elevated temperature, for example, greater than or equal to 500° C., preferably, 500 to 550° C.

Likewise, the passivating can be a continuous passivating that can occur by continuously introducing a sulfur stream to the reactor. In this case, the sulfur stream can be introduced such that the combined volume of the sulfur stream and the reactant stream(s) comprises 0.1 to 8 vol % sulfur, preferably, 0.25 to 0.5 vol % sulfur, more preferably, 0.5 to 3 vol % sulfur. It is understood that the sulfur stream can be added to the reactor separately from the reactant stream(s) or can be combined with the reactant stream(s) prior to addition to the reactor.

Set forth below are some embodiments of the present method of making syngas.

Embodiment 1

A method of making syngas in a metal reactor comprising: introducing carbon dioxide and hydrogen to the metal reactor in the presence of a catalyst to form the syngas, wherein the metal reactor comprises nickel and wherein the carbon dioxide and the hydrogen are in physical contact with a wall of the metal reactor; and passivating the nickel with a sulfur containing compound.

Embodiment 2

The method of Embodiment 1, wherein the passivating comprises an initial passivating that occurs prior to the introducing of the carbon dioxide and hydrogen and/or an intermittent passivating that occurs after the introducing of the carbon dioxide and hydrogen.

Embodiment 3

The method of Embodiment 2, wherein the initial passivating and/or the intermittent passivating occurs for 4 to 24 hours.

Embodiment 4

The method of any of Embodiments 2-3, wherein the passivating comprises initial passivating and the method further comprising the step of adding the catalyst to the metal reactor after the initial passivating.

Embodiment 5

The method of any of Embodiments 2-4, wherein the intermittent passivating occurs after a pressure in the metal reactor is less than or equal to 0.1 MPa.

Embodiment 6

The method of any of Embodiments 2-5, further comprising introducing an oxygen stream at a temperature of greater than or equal to 500° C. during or after the intermittent passivating.

Embodiment 7

The method of Embodiment 6, wherein the oxygen stream comprises air.

Embodiment 8

The method of any of Embodiments 2-7, further comprising removing the catalyst prior to the intermittent passivating.

Embodiment 9

The method Embodiment 1, wherein the passivating comprises a continuous passivating that occurs simultaneously with the introducing of the carbon dioxide and hydrogen by introducing the sulfur containing compound to the reactor in a sulfur stream.

Embodiment 10

The method of Embodiment 9, wherein the passivating comprises an initial passivating that occurs prior to the introducing of the carbon dioxide and hydrogen.

Embodiment 11

The method of Embodiment 10, further comprising the step of adding the catalyst to the metal reactor after the initial passivating.

Embodiment 12

The method of any of Embodiments 9-11, wherein the sulfur containing compound is introduced in an amount of 0.1 to 8 vol % based on the total volume introduced to the reactor.

Embodiment 13

The method of any of Embodiments 1-12, wherein the reactor is an adiabatic reactor.

Embodiment 14

The method of any of Embodiments 1-13, wherein the introducing occurs at a temperature of 650 to 800° C.

Embodiment 15

The method of any of Embodiments 1-14, wherein the introducing occurs at a temperature of 730 to 750° C.

Embodiment 16

The method of any of Embodiments 1-15, wherein the introducing occurs at a pressure of 0.1 to 6 MPa.

Embodiment 17

The method of any of Embodiments 1-16, wherein the reactor comprises stainless steel.

Embodiment 18

The method of any of Embodiments 1-17, wherein the reactor comprises 0.1 to 20 wt % nickel.

Embodiment 19

The method of any of Embodiments 1-18, wherein the carbon dioxide and the hydrogen are introduced at a $CO_2:H_2$ ratio of 1:1 to 1:10.

Embodiment 20

The method of any of Embodiments 1-13, wherein the syngas has a $H_2:CO$ ratio of 0.1 to 10.

Embodiment 21

The method of any of Embodiments 1-20, wherein the catalyst comprises a metal oxide catalyst.

Embodiment 22

The method of any of Embodiments 1-21, wherein the metal comprises Cr, Mn, Sn, W, V, Mo, La, Ce, Pb, Mg, Ca, K, W, Cu, or a combination comprising one or more of the foregoing.

Embodiment 23

The method of any of Embodiments 1-22, wherein the catalyst comprises a support.

Embodiment 24

The method of any of Embodiments 1-23, further comprising using the syngas in a methanol production reaction.

Embodiment 25

The method of any of Embodiments 1-24, further comprising combining the syngas with a second syngas.

All ranges disclosed herein are inclusive of the endpoints, and the endpoints are independently combinable with each other (e.g., ranges of "up to 25 wt %, or, more preferably, 5 to 20 wt %," is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. Disclosure of a narrower range in addition to a broader range is not a disclaimer of the broader range. This application claims priority to U.S. Patent application 61/902,542 filed on Nov. 11, 2013.

While particular embodiments have been described, alternatives, modifications, variations, improvements, and substantial equivalents that are or may be presently unforeseen may arise to Applicants or others skilled in the art. Accordingly, the appended claims as filed and as they may be amended are intended to embrace all such alternatives, modifications variations, improvements, and substantial equivalents.

We claim:

1. A method of making syngas in a metal reactor comprising:
introducing carbon dioxide and hydrogen to the metal reactor in the presence of a catalyst to form the syngas, wherein a wall of the metal reactor comprises nickel and wherein the carbon dioxide and the hydrogen are in physical contact with the wall of the metal reactor; and
passivating the nickel in the reactor walls with a sulfur containing compound.

2. The method of claim 1, wherein the passivating comprises an initial passivating that occurs prior to the introducing of the carbon dioxide and hydrogen and/or an intermittent passivating that occurs after the introducing of the carbon dioxide and hydrogen.

3. The method of claim 2, wherein the initial passivating and/or the intermittent passivating occurs for 4 to 24 hours.

4. The method of claim 2, wherein the passivating comprises initial passivating and the method further comprises adding the catalyst to the metal reactor after the initial passivating.

5. The method of claim 2, wherein the intermittent passivating occurs after a pressure in the metal reactor is less than or equal to 0.1 MPa.

6. The method of claim 2, further comprising introducing an oxygen stream at a temperature of greater than or equal to 500° C. during or after the intermittent passivating.

7. The method of claim 2, further comprising removing the catalyst prior to the intermittent passivating.

8. The method claim 1, wherein the passivating comprises a continuous passivating that occurs simultaneously with the introducing of the carbon dioxide and hydrogen by introducing the sulfur containing compound to the reactor in a sulfur stream.

9. The method of claim 8, wherein the passivating comprises an initial passivating that occurs prior to the introducing of the carbon dioxide and hydrogen.

10. The method of claim 9, further comprising adding the catalyst to the metal reactor after the initial passivating.

11. The method of claim 8, wherein the sulfur containing compound is introduced in an amount of 0.1 to 8 vol % based on the total volume introduced to the reactor.

12. The method of claim 1, wherein the reactor is an adiabatic reactor.

13. The method of claim 1, wherein the reactor comprises stainless steel.

14. The method of claim 1, wherein reactor comprises 0.1 to 20 wt % nickel.

15. The method of claim 1, wherein the carbon dioxide and the hydrogen are introduced at a $CO_2:H_2$ ratio of 1:1 to 1:10.

16. The method of claim 1, wherein the syngas has a $H_2:CO$ ratio of 0.1 to 10.

17. The method of claim 1, wherein the catalyst comprises a metal oxide catalyst.

18. The method of claim 1, wherein the metal comprises Cr, Mn, Sn, W, V, Mo, La, Ce, Pb, Mg, Ca, K, W, Cu, or a combination comprising one or more of the foregoing.

19. The method of claim 1, further comprising using the syngas in a methanol production reaction.

20. The method of claim 1, further comprising combining the syngas with a second syngas from a different syngas source.

* * * * *